United States Patent [19]

Cohen

[11] Patent Number: 5,125,908
[45] Date of Patent: Jun. 30, 1992

[54] HYPODERMIC SYRINGE WITH PROTECTIVE HOLDER

[76] Inventor: Milton J. Cohen, 10823 Burbank Dr., Potomac, Md. 20854

[21] Appl. No.: 601,211

[22] Filed: Oct. 19, 1990

[51] Int. Cl.⁵ .............................................. A61M 5/32
[52] U.S. Cl. ................................ 604/196; 604/110; 604/192
[58] Field of Search .................... 604/192, 195–198, 604/263, 110, 187, 220; 128/919

[56] References Cited

U.S. PATENT DOCUMENTS

| | | |
|---|---|---|
| 3,413,974 | 12/1968 | Cohen . |
| 3,682,174 | 8/1972 | Cohen . |
| 3,757,779 | 9/1973 | Rovinski . |
| 4,009,716 | 3/1977 | Cohen . |
| 4,479,801 | 10/1984 | Cohen . |
| 4,564,054 | 1/1986 | Gustavsson ........................ 141/329 |
| 4,747,829 | 5/1988 | Jacob et al. ........................ 604/110 |
| 4,790,822 | 12/1988 | Haining ............................... 604/110 |
| 4,801,295 | 1/1989 | Spencer .............................. 604/198 |
| 4,850,994 | 7/1989 | Zerbst et al. ....................... 604/198 |
| 4,915,699 | 4/1990 | Kornberg ............................ 604/195 |
| 4,919,652 | 4/1990 | Alter et al. .......................... 604/110 |
| 4,923,445 | 5/1990 | Ryan .................................... 604/195 |
| 4,955,869 | 9/1990 | Bin ...................................... 604/195 |
| 4,957,490 | 9/1990 | Byrne et al. ........................ 604/197 |
| 4,995,870 | 2/1991 | Baskas ................................ 604/110 |
| 4,995,874 | 2/1991 | Strickland .......................... 604/195 |
| 5,007,903 | 4/1991 | Ellard ................................. 604/195 |
| 5,024,616 | 6/1991 | Ogle .................................... 604/192 |
| 5,030,208 | 7/1991 | Novacek et al. ................... 604/195 |
| 5,069,225 | 12/1991 | Okamura ........................... 128/765 |

FOREIGN PATENT DOCUMENTS 1008915  11/1965  United Kingdom ............... 604/197

Primary Examiner—C. Fred Rosenbaum
Assistant Examiner—Mark O. Polutta
Attorney, Agent, or Firm—Rockey and Rifkin

[57] ABSTRACT

An improved hypodermic syringe employs a syringe holder which surrounds the syringe barrel, including the needle, both before and after injection. The syringe holder encases the operable parts of the syringe prior to use. One embodiment employs a plunger having a plunger lock adapted to engage a counterlock in a rubber support, which holds the needle in place. When the plunger is fully compressed to inject the liquid, the plunger lock engages the counterlock, allowing the needle to be retracted into the syringe holder by pulling the plunger. In an alternate embodiment, a conventional one-piece plunger is used. After injection, the needle is retracted into the holder by grasping and pulling the syringe barrel.

5 Claims, 4 Drawing Sheets

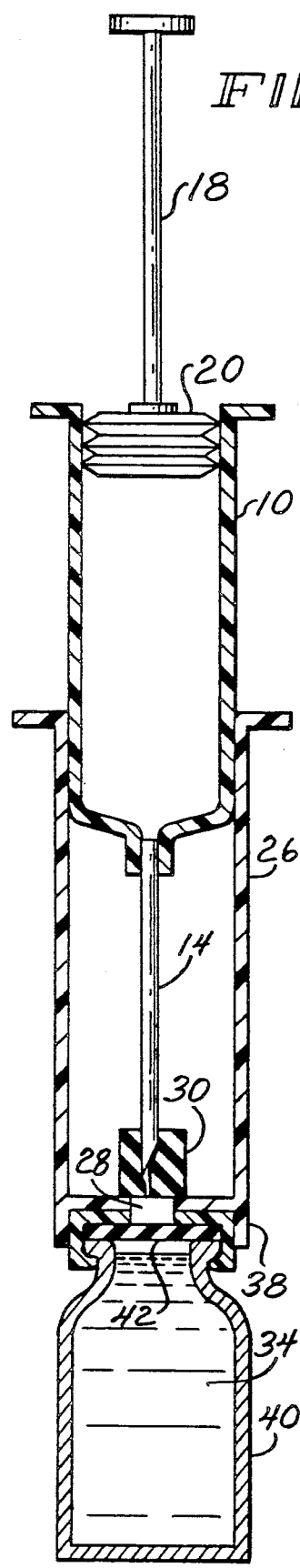
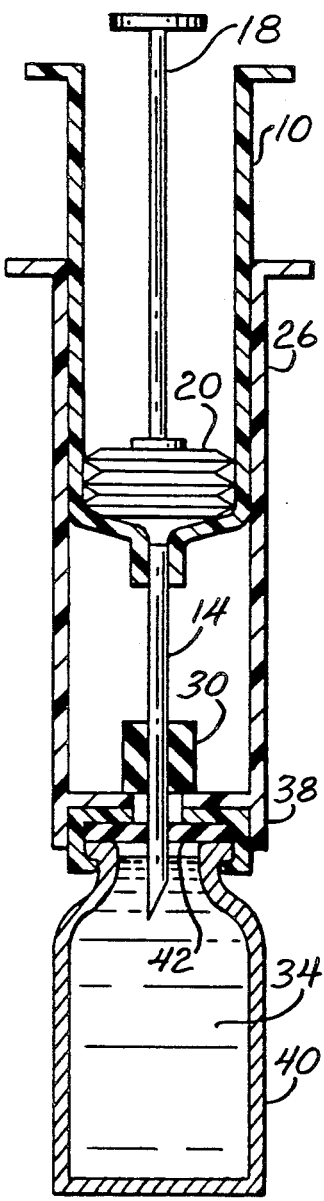
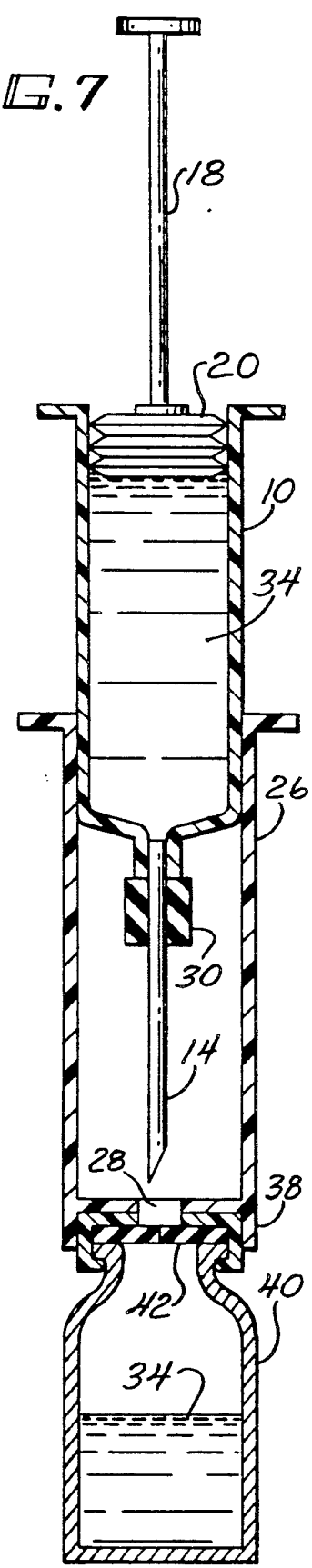

HYPODERMIC SYRINGE WITH PROTECTIVE HOLDER

BACKGROUND AND OBJECTS OF THE INVENTION

The present invention relates to a syringe for injecting medicaments and other liquids, and more particularly, to syringe that includes a protective holder to prevent injury to the syringe user.

Disposable hypodermic syringes are disclosed in U.S. Pat. Nos. 3,401,693, 3,682,174, 3,757,779, 3,413,974, have a barrel fitted with an axially displacable plunger in sealing engagement with the barrel. A hollow needle is attached to one end of the barrel. When the plunger is compressed, liquid in the barrel is ejected through the needle.

Normally, the syringe includes a needle cap which covers the needle to prevent inadvertent injury when the syringe is not in use. However, the needle cap is removed prior to use, exposing the needle. Exposure of the needle results in an increased possibility of injury to a health professional or the patient. A syringe which may be used without exposing the needle before use is desirable.

Accordingly, it is an object of the invention to provide a hypodermic syringe which may be used after exposing the needle from a protective holder.

It is a further object of the invention to provide such a syringe which facilitates ease in destruction of the needle after use.

It is another object of the invention to provide such a syringe which may be inexpensively manufactured.

It is yet another object of the invention to provide such a syringe which is of durable and reliable construction.

These objects, as well as others, will become apparent to those skilled in the art from the detailed description of the invention provided below.

SUMMARY OF THE INVENTION

The present invention employs a syringe holder which surrounds the syringe, including the needle, both before and after operation. The syringe holder encases the operable parts of the syringe prior to use. The holder has an aperture at one end to allow passage of the needle during use. The needle is then retracted into the syringe holder to prevent after-use injury from accidental sticking of the syringe operator or patient.

One embodiment employs a two-piece plunger, one end thereof having a plunger lock adapted to engage a counterlock in a rubber support, which holds the needle in place. When the plunger is fully compressed to inject the liquid, the lock engages the counterlock, allowing the needle to be retracted into the syringe holder by pulling the plunger.

An alternate embodiment employs a standard syringe having a conventional one-piece plunger. After injection, the needle is retracted into the holder by grasping and pulling the syringe barrel.

BRIEF DESCRIPTION OF THE DRAWINGS

FIG. 5 is a view similar to FIG. 1 showing the syringe of the present invention prior to being filled from a vial of liquid.

FIG. 6 is a view similar to FIG. 5 showing the syringe being filled from the vial.

FIG. 7 is a view similar to FIG. 5 and FIG. 6 showing the syringe retracted into the syringe after being filled from the vial.

DETAILED DESCRIPTION OF A PREFERRED EMBODIMENT

Figure 1:
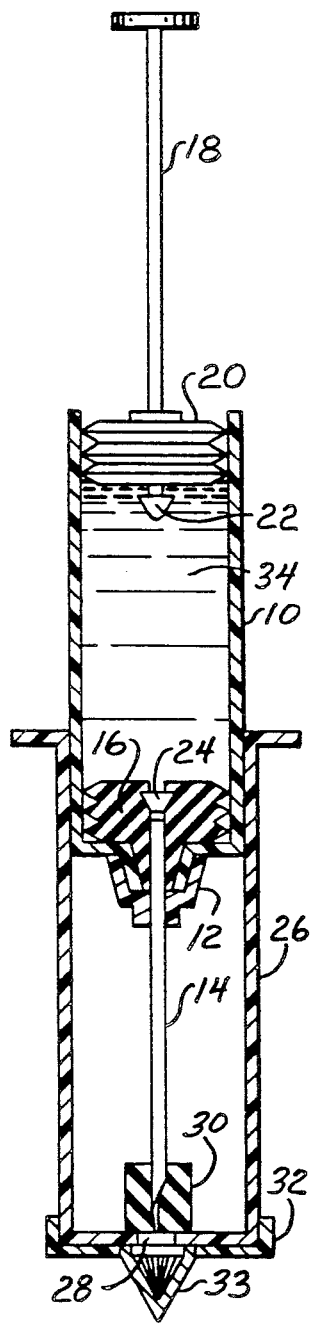
FIG. 1 is a side view in partial section of one embodiment of the present invention showing the syringe as stored prior to use.

Referring to the drawings, a preferred embodiment of the present invention is shown in FIG. 1. A hollow, cylindrical syringe barrel 10 has a needle hub 12 disposed at one end. A hollow needle 14 passes through an aperture in the needle hub 12. The needle is secured to the barrel 10 by a rubber support 16, which is disposed within the barrel 10. A plunger shaft 18 is disposed for slidable movement within the barrel 10. The plunger shaft 18 is secured to a rubber sealing ring 20, which is dimensioned to seal the barrel 10 during operation of the syringe. The end of the plunger shaft is formed into a plunger lock 22. As will be described hereinafter, the plunger lock 22 is dimensioned for engagement in a counterlock 24 formed in the rubber needle support 16.

The barrel 10 is mounted for slidable movement inside a cylindrical syringe holder 26. The syringe holder 26 has an aperture 28 to allow passage of the needle 14 during use of the syringe. A rubber plug 30 occludes the point of the needle, further reducing the chance of accidental injury prior to use of the syringe. Additionally, the plug 30 covers the aperture 28 and protects the needle 14 prior to use of the syringe. A cover 32 is removably secured over the end of the holder 26. The cover 32 is removed prior to use of the syringe.

Figure 2:
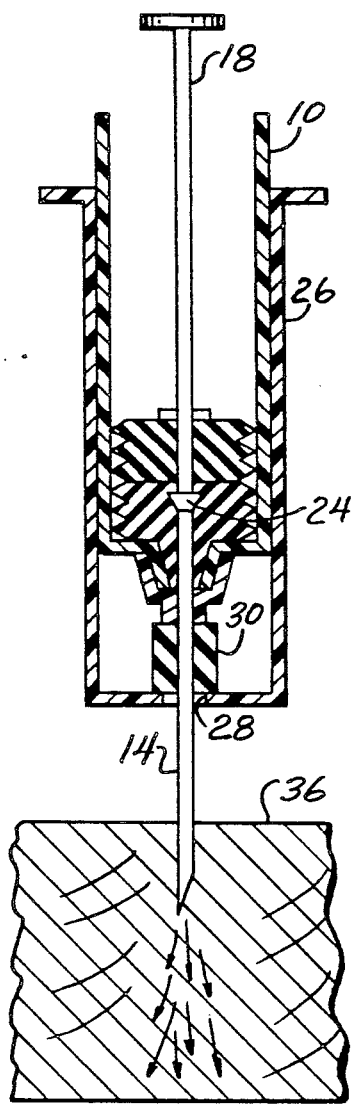
FIG. 2 is a view similar to FIG. 1 showing the syringe in use.

In operation, the syringe is pre-filled with an injectable liquid 34 as shown in FIG. 1. The cover 32 is removed from the holder 26. The barrel 10 is moved downward to expose the needle. This may be accomplished by grasping the barrel 10 and pushing downward. As the barrel travels downward, the needle 14 passes through the plug 30 and into the tissue 36 to be injected (FIG. 2). The plug 30 continues to slide up the needle 14 until the plunger is fully compressed, ultimately coming to rest against the needle hub 12. Thus, displacement of the plug 30 to expose the needle 14 requires no additional effort by the syringe user.

Figure 3:
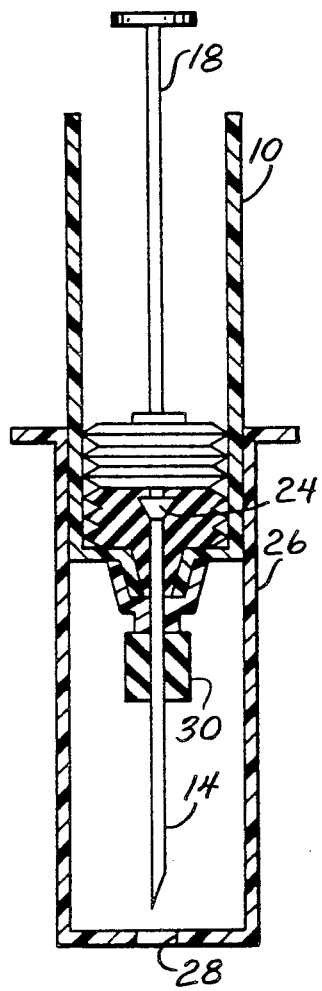
FIG. 3 is a view similar to FIG. 1 and FIG. 2 showing the syringe retracted into the syringe holder after use.

As the plunger 18 is compressed, the liquid 34 is injected into the tissue 36. When the plunger 18 is fully depressed, the plunger lock 22 engages the counterlock 24. After the injection is complete, the plunger 18 is retracted as shown in FIG. 3. The engagement of the plunger lock 22 with the counterlock 24 causes the needle 14 to be retracted into the holder 26. Thus, the needle is not exposed during use of the syringe, minimizing the chance of accidental sticking of the syringe user or patient.

Figure 4:
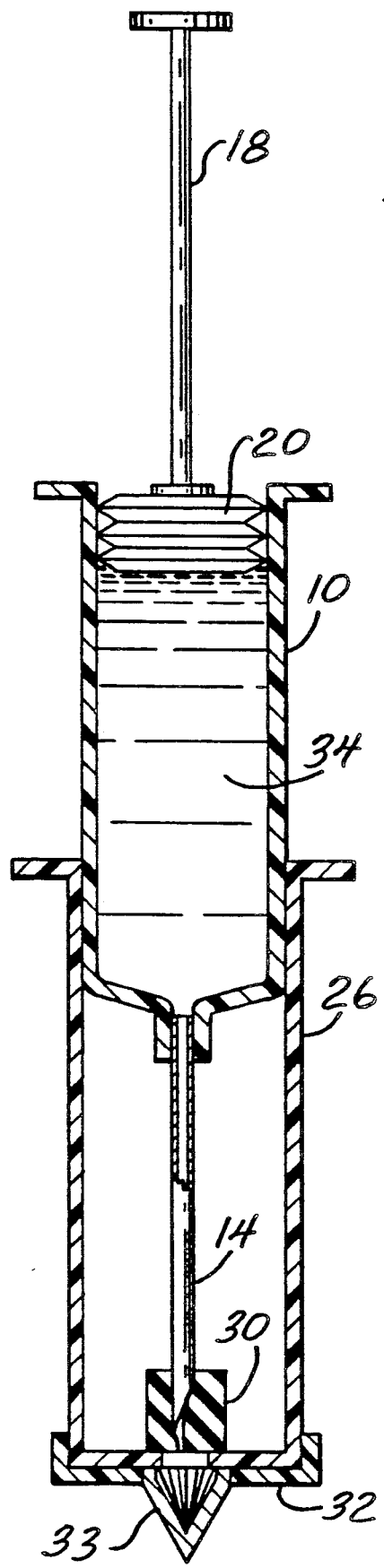
FIG. 4 is a side view in partial section of an alternate embodiment of the present invention.

FIG. 4 shows an alternate embodiment of the invention having a conventional one-piece plunger without a plunger lock and counterlock. This embodiment operates similarly to the embodiment described above; however, pulling the plunger will not retract the needle into the holder 26 in this embodiment. Instead, the barrel 10 is grasped and pulled by the syringe operator to accomplish this.

As will be apparent to one of ordinary skill in the art, a modification of the process just described may be employed to fill an empty syringe with liquid. FIG. 5 shows an embodiment of the invention having an annular lip portion 38 extending from the bottom of the syringe holder 26. The lip portion 38 is adapted to cooperate with a vial 40, which contains liquid 34. The vial 40 is sealed by a stopper 42. The syringe of is positioned adjacent to the vial 40 so that the lip portion 38 covers the top of the vial 40. The lip portion 38 prevents accidental slippage of the syringe while it is being filled with liquid.

Next, the plunger of the syringe is compressed, as shown in FIG. 6. The barrel 10 is then pushed downwardly, causing the needle 14 to pierce the stopper 40. When the plunger is retracted, the barrel 10 fills with the liquid 34. The needle 14 is then retracted into the holder 26, as previously described. As shown in FIG. 7, the syringe may then be safely maintained until needed. If the syringe employs the two-piece plunger previously described with reference to FIG. 1, FIG. 2 and FIG. 3, the plunger should be displaced to a point just prior to engagement of the lock with the counterlock prior to insertion of the needle into the vial.

The present invention facilitates easy and efficient destruction of the needle 14 to prevent subsequent injury, reduce the likelihood that the syringe will be used for illicit purposes and prevent the spread of diseases that are transmitted through reuse of syringes. At the same time, the syringe of the present invention minimizes the risk of injury to the syringe operator during destruction of the needle.

Figure 8:
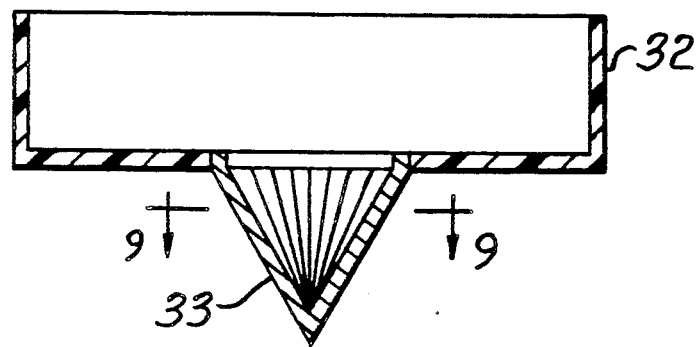
FIG. 8 is a side view of a cap having means for destroying the efficacy of the needle after use.
Figure 9:
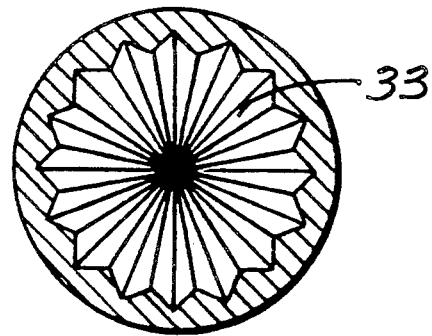
FIG. 9 is a plan view of the cap shown in FIG. 8.

After the syringe is used and the needle retracted into the protective holder 26, the cover 32 is replaced on the end of the syringe holder. As shown in FIG. 8, the cover 32 has a centrally disposed metal conical projection 33 attached thereto. The inner surface of the conical projection is serrated, as may be clearly seen from FIG. 9, which shows a plan view of the cover 32. The efficacy of the needle 14 may then be destroyed by displacing the needle (as described above) into contact with the serrated edges of the aperture in the replacement cover and twisting the barrel of the syringe.

The present invention has been described with respect to certain embodiments and conditions, which are not meant to limit the invention. Those skilled in the art will understand that variations from the embodiments and conditions described herein may be made without departing from the invention as set forth in the appended claims.

What is claimed is:

1. A hypodermic syringe of the type used to inject liquid, comprising:
  a) a barrel for receiving liquid;
  b) a hollow needle mounted in a needle support at one end of the barrel, said needle cooperating with said barrel to allow passage of liquid from said barrel through said needle;
  c) a plunger supported in said barrel by a rubber sealing ring, said rubber sealing ring forming a liquid-tight seal with said barrel and allowing slidable, reciprocal movement of said plunger within said barrel;
  d) means for locking said plunger to said needle support when said plunger is displaced substantially fully into said barrel;
  e) a protective holder dimensioned to slidably receive said barrel where said barrel is slidably movable in said holder from an initial retracted position where the needle is within the holder and said barrel is full of liquid to an extended position where the needle projects from the holder for injecting the liquid and then to a final retracted position where the liquid has been expelled from the barrel and the needle is within the holder, said holder being open at one end to receive said barrel and the opposite end thereof having portions defining an aperture through which the needle can pass when said cylinder is slidably moved in the holder; and
  f) a rubber plug covering the aperture to occlude the needle and to isolate the needle from the user in both the initial retracted and final retracted positions.

2. The syringe of claim 1 further including means for destroying the efficacy of said needle.

3. The syringe of claim 2 wherein said means for destroying includes a cover removably secured to said protective holder, said cover having a centrally disposed conical portion extending downwardly therefrom, the inner surface of said conical portion being serrated to facilitate the destruction of the efficacy of said needle.

4. The syringe of claim 1 wherein said protective holder further includes means for engaging a vial, said vial containing said liquid.

5. The syringe of claim 4 wherein said means for engaging includes an annular lip portion extending downwardly from said protective holder.

* * * * *